United States Patent [19]

Bzdula

[11] 4,434,233
[45] Feb. 28, 1984

[54] METHOD OF TESTING OIL FOR IONIC CONTAMINANTS

[75] Inventor: Joseph A. Bzdula, Fulton, N.Y.

[73] Assignee: Carrier Corporation, Syracuse, N.Y.

[21] Appl. No.: 239,920

[22] Filed: Mar. 3, 1981

[51] Int. Cl.³ .............................................. G01N 27/06
[52] U.S. Cl. ........................................ 436/60; 62/125; 62/470; 324/439; 436/150
[58] Field of Search ...................... 23/230 HC, 230 R; 324/439; 62/125, 470; 436/150, 60, 61, 139

[56] References Cited

U.S. PATENT DOCUMENTS

| | | | |
|---|---|---|---|
| 2,122,578 | 7/1938 | McMaster et al. | 324/439 X |
| 2,155,051 | 4/1939 | Kagi | 62/470 X |
| 2,782,151 | 2/1957 | Suthard | 23/230 HC X |
| 3,271,111 | 9/1966 | Boyd, Jr. et al. | 23/230 R |
| 4,009,998 | 3/1977 | Benningfield, Jr. | 23/230 R |
| 4,023,931 | 5/1977 | Wolfgram | 23/230 R |
| 4,288,402 | 9/1981 | Ellis | 23/230 HC X |

*Primary Examiner*—Arnold Turk
*Attorney, Agent, or Firm*—David L. Adour

[57] ABSTRACT

A method of testing oil for ionic contaminants is disclosed. The method comprises isolating a sample of the oil to be tested and mixing it with an equal weight of distilled water to dissolve ionic contaminants in the oil sample into the distilled water. Then, the contaminated water is separated from the mixture and its conductivity is determined. An alternative to separating the contaminated water is to use a surfactant to form an oil in water emulsion with the oil sample and the distilled water. The conductivity of the emulsion is determined directly. The magnitude of the conductivity directly indicates the amount of ionic contaminants present in the oil being tested. This method is especially suitable for determining the level of ionic contamination in the refrigerant of a refrigeration system of the type having a compressor drive which is lubricated with oil and wherein there is contact between the refrigerant and the oil. Ionic contaminants in the refrigerant of a refrigeration system are direct indicators of the presence of excessive amounts of water and/or certain undesirable metals in the refrigerant since these substances cause the formation of ionic contaminants in the refrigerant.

13 Claims, 1 Drawing Figure

OIL ANALYSIS BY SPECIFIC CONDUCTANCE

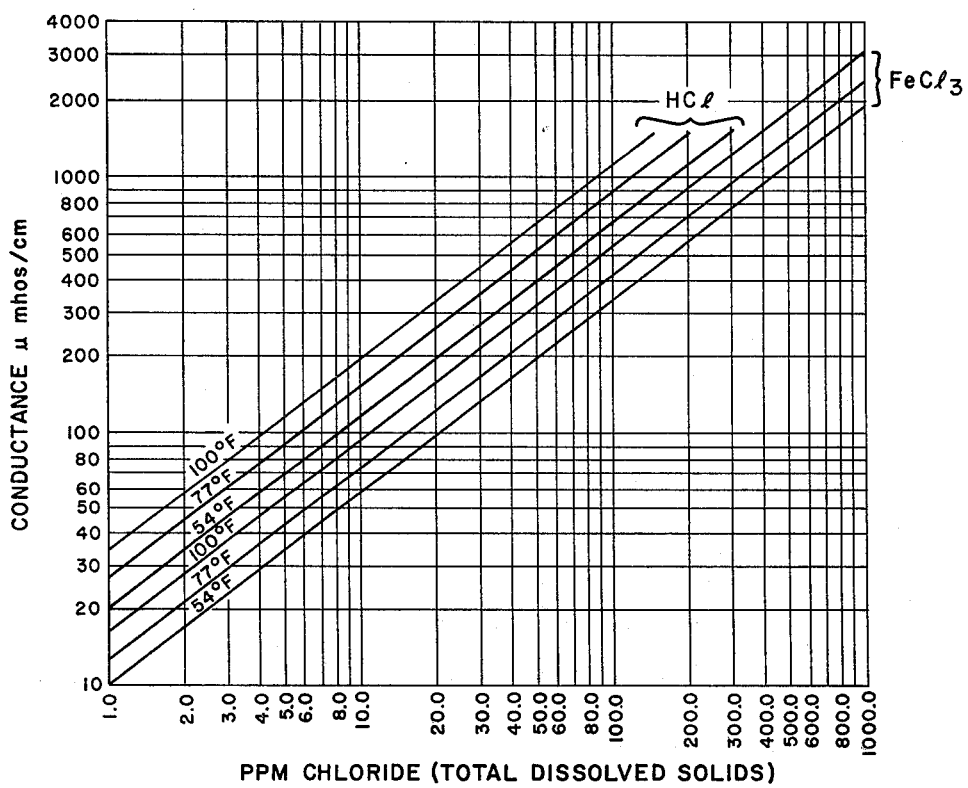
OIL ANALYSIS BY SPECIFIC CONDUCTANCE

METHOD OF TESTING OIL FOR IONIC CONTAMINANTS

BACKGROUND OF THE INVENTION

This invention relates to a method of testing oil for ionic contaminants and for determining contamination of a refrigerant in a refrigeration system. More particularly this invention relates to a method of testing oil for ionic contaminants by measuring the conductance of water extracts of the oil. The invention is especially useful for testing the lubricating oil for a compressor drive of a refrigeration system of the type wherein there is contact between the refrigerant from the refrigeration system and the compressor drive lubricating oil. Testing this lubricating oil for ionic contaminants provides a method of testing the refrigerant for ionic contaminants because ionic contaminants present in the refrigerant also will be present in the lubricating oil due to the contact between the refrigerant and the oil.

Oil is used in a variety of applications such as a working fluid or as a lubricating fluid where the oil is within a closed system where it should be maintained in a relatively pure state to perform properly its intended function. Ionic contaminants in the oil indicate that the system is not functioning properly. Therefore, it is desirable to provide a method of testing oil for ionic contaminants.

The presence of ionic contaminants in the oil of a closed system may indicate a variety of problems depending on the type of system within which the oil is being used. For example, if the oil is being used as a hydraulic fluid then ionic contaminants in the oil may indicate a break-down of the oil. If the oil is being used solely as a lubricating fluid then ionic contaminants in the oil may indicate a physical break-down of the mechanical parts which are lubricated by the oil. Ionic contaminants in the lubricating oil for a compressor drive of a refrigeration system of the type having refrigerant from the refrigeration system in contact with the compressor drive lubricating oil, may indicate the presence of a water leak into the refrigerant of the refrigeration system. This is possible because excess water in refrigerant forms hydrogen chloride which is an ionic contaminant. This hydrogen chloride is found in the compressor drive lubricating oil because of the contact between the refrigerant of the refrigeration system and the compressor drive lubricating oil. Thus, testing this compressor lubricating oil for ionic contaminants can provide a quick, easy, inexpensive, and reliable method of detecting a water leak into the refrigerant of a refrigeration system, and the extent to which water has accumulated in the system.

Refrigerant in a typical refrigeration system can absorb a certain amount of water without substantially affecting the operation of the refrigeration system. Occasionally, some water may be present in the refrigerant due to moist air leaking into low pressure parts of the refrigeration system or due to small leaks in the heat exchanger tubing of the refrigeration system. The small leaks are caused by wear and tear of the tubing after prolonged use, corrosion of the tubing joints, and other such conditions. Typically, purging means are included as part of the refrigeration system to remove non-condensibles and water. However, when the amount of water introduced into the refrigerant exceeds the saturation level of the refrigerant then a more serious problem is posed to the refrigeration system. Excess water indicates that there may be a significant water leak in the refrigeration system. Excess water which cannot be absorbed by the refrigerant forms a water layer on liquid portions of the refrigerant in the refrigeration system resulting in the formation of hydrogen chloride. Hydrogen chloride is extremely reactive with materials, such as iron and copper, used in constructing a refrigeration system. Hydrogen chloride reacts with these materials to cause corrosion and deterioration of the materials.

Prior art methods of testing for water in refrigerant have included a colorimetric method and a hygroscopic salt method. According to the colorimetric method, refrigerant is circulated through a moisture sensitive indicator which changes color upon contact with moisture. The indicator senses excess water which cannot be absorbed by the refrigerant. According to the hygroscopic salt method, an electrode made of water absorbing salt is inserted in the refrigerant system so that when the electrode is in contact with water an electronic circuit is triggered which measures the conductance of the probe. Theoretically, the measured conductance is a direct indication of the amount of water in the refrigerant system.

These prior art methods of testing for water in refrigerant depend on where the sample of refrigerant to be tested is taken from the refrigeration system. Refrigerant is continually changing phase and moving through the refrigeration system whereby the water content of the refrigerant is not constant at all locations within the system. Also, since excess water floats on top of the liquid refrigerant at various places within the refrigeration system, any sample of refrigerant taken from a location, other than where this excess water is present, will give an indication of water content which is lower than the actual water content present in the system. Thus, choosing a sampling location is of critical importance when using these prior art methods of testing for water in refrigerant. In practice no sampling location can provide a representative sample of the refrigerant at all times. In the present invention a small portion of the refrigerant is constantly in contact with the compressor drive lubricating oil of the refrigeration system and deposits contaminants in this oil. Since the portion of refrigerant in contact with the oil is constantly changing, the amount of contaminants in the oil tends to be an average of the contaminants in the refrigerant of the refrigeration system.

SUMMARY OF THE INVENTION

Therefore, it is an object of the present invention to test oil for ionic contaminants.

Another object of the present invention is to provide a simple, reliable method of determining amounts of ionic contaminants in a refrigeration system.

A further object of the present invention is to provide a method of testing for the presence of excessive water and/or the presence of certain metals which form ionic contaminants in the refrigerant of a refrigeration system of the type having a compressor drive lubricated by oil whereby there is contact between the refrigerant and the oil.

These and other objects of the present invention are attained by a method which comprises isolating a sample of the oil to be tested, mixing the oil sample with an approximately equal weight of distilled water to dissolve ionic contaminants in the oil sample into the distilled water and separating the contaminated water from the oil sample. The separating step can be eliminated by mixing a relatively small amount of surfactant, an amount of distilled water which is approximately equal in volume to the isolated oil sample, and the oil to form an emulsion. After separation, or after the emulsion is formed, the conductance of the contaminated water is determined. If the contaminated water has a conductivity greater than the conductivity of distilled water at the same temperature this indicates that ionic contaminants are present in the oil being tested. The amount of ionic contaminants present in the oil being tested is directly indicated by the magnitude of the conductivity of the contaminated water. Changes in the concentration of ionic contaminants in the oil being tested are detected by making a series of conductivity determinations at different times within a selected time period.

BRIEF DESCRIPTION OF THE DRAWING

The figure shows a graph of the conductivity of a distilled water sample as a function of chloride concentration and as a function of temperature for two different kinds of chlorides which are dissolved in the distilled water.

DESCRIPTION OF THE PREFERRED EMBODIMENTS

Generally, the present invention is a method of testing oil for ionic contaminants. The method is especially useful for testing for ionic contaminants in paraffinic, naphthenic, and synthetic oils. However, the method is not limited to use with these particular types of oil.

The presence of ionic contaminants in oil is usually an indication that there is a problem in the system in which the oil is being used. The kind of problem depends on the particular system under consideration. For example, if the oil is used as a working fluid or as a lubricating fluid in a closed system the presence of ionic contaminants in the oil may indicate a break-down of the oil or a mechanical problem with the parts being lubricated. The present invention is particularly useful for testing the lubricating oil for a compressor drive of a refrigeration system. The lubricating oil is tested for ionic contaminants to determine if there is a water leak and/or a mechanical problem in the refrigeration system.

A refrigeration system of the type under consideration typically includes, a compressor, an evaporator, and a condenser, interconnected to form a closed circuit for the flow of refrigerant. Liquid refrigerant is passed into the evaporator and vaporized therein as heat is extracted from water passing through pipes in heat exchange relation with the refrigerant. Then, the compressor withdraws the vaporous refrigerant from the evaporator and forwards it at a higher pressure to the condenser where the refrigerant is once again converted to the liquid state as it passes in heat exchange relation with cooling water in tubes submerged in the vaporous and liquid refrigerant. It is necessary to provide a lubrication system for the purpose of lubricating the moving parts of the compressor and the motor employed to drive the compressor. By design and normal leakage the refrigerant of the refrigeration system and the compressor drive lubricating oil come in contact. A mechanism is usually provided for withdrawing a portion of the refrigerant-lubricant mixture and for vaporizing the refrigerant constitute of the mixture. Then, the lubricant is automatically returned to the lubrication system and the refrigerant to the refrigeration system. Therefore, there is a continual exchange of the refrigerant in the oil.

Testing the compressor lubricating oil generally for ionic contaminants results in a positive test whenever any type of ionic contaminants are present in the oil. Therefore, the method of testing oil for ionic contaminants according to the principles of the present invention may only generally indicate the presence of a problem within a refrigeration system. Once contaminants are detected it is then necessary to investigate further to determine what kinds of ionic contaminants are present and the source of these ionic contaminants. However, the reliable, quick, easy, and inexpensive features of the present invention in determining that there is a problem which should be investigated is of great benefit. Also, in many instances the particular kind of ionic contaminant detected and its probable origin may be determined without further investigation as will be discussed in the following detailed description of steps comprising a preferred method of practicing the present invention. Generally, the presence of iron chloride and/or copper chloride in the oil indicates either a mechanical problem within the refrigeration system, such as a compressor drive bearing failure or a water leak of sufficient magnitude to result in refrigerant hydrolysis. The presence of hydrogen chloride in the oil is a strong indication of excess water and refrigerant hydrolysis.

The sample size of the compressor lubricating oil tested should be small relative to the total capacity of the lubricating system. A 50 gram sample of oil is sufficient but the particular amount is not critical. The oil sample is placed in a container, such as a separatory funnel, and is brought to room temperature which is preferably a temperature of approximately 70° F. or above. The exact temperature of the oil sample is not critical as long as the oil sample is at a temperature at which it can be mixed with distilled water. However, it is preferable to have the oil sample at a temperature of at least approximately 70° F. to facilitate mixing of the oil sample with the distilled water.

An approximately equal weight amount of distilled water is mixed with the oil sample to dissolve ionic contaminants in the oil into the distilled water. Preferably, the distilled water is added slowly to the container containing the oil sample to allow the safe venting of any gases which may be generated. One way of mixing the distilled water and the oil sample is to shake the substances in a separatory funnel. Stirring or any other way of mixing is acceptable. The key feature is that the mixing occurs whereby the distilled water and oil are brought into intimate physical contact so that ionic contaminants present in the oil sample are dissolved into the distilled water.

The exact temperature of the distilled water is not critical, however, hot water allows the oil sample and the distilled water to be easily mixed. Also, the rate at which ionic contaminants are dissolved from the oil sample into the distilled water depends on the water temperature. Dissolution occurs faster at higher temperatures. A convenient temperature for the distilled water is 200° F. because this temperature is easily attained by heating the distilled water almost to its boiling temperature or by heating the distilled water to its boiling temperature and then allowing it to cool for several minutes. This may be done at the site where the compressor oil is being tested.

The exact amount of distilled water used is not critical but it should be enough to allow for adequate mixing to bring the constituents of the oil sample into close physical contact with the distilled water. An equal weight of distilled water or any greater amount insures that the close physical contact is easily achieved. If a substantially lesser amount of distilled water is used there is a possibility that the distilled water can become saturated with contaminants and not represent the actual concentration of ionic contaminants present in the oil sample.

After mixing, the distilled water with contaminants dissolved therein is separated from the oil sample. A convenient way of separating this contaminated water is by holding the mixture stationary in a separatory funnel to allow the contaminated water to settle out of the mixture due to the difference in specific gravity between the oil sample and the contaminated water. However, filtering or any other suitable separation technique can be used.

After separation, the contaminated water is filtered to remove any residual oil which is present. It is preferred to use filtering since residual oil may coat the electrodes of a conductivity probe used to determine the conductance of the contaminated water. This could result in a false conductivity reading. Therefore, it is preferable to eliminate as much of the residual oil as possible before testing the sample for its conductivity. However, it should be understood that filtering is not required because usually a single conductivity determination does not result in sufficient coating of the electrodes to present a problem. However, if the same conductivity cell is used to make many conductivity determinations it is desirable to use filtering to circumvent the coating problem.

The resistance of the contaminated water is the parameter which is actually measured. A portion of the contaminated water is used to make the resistance measurement by using a conventional conductivity cell. The temperature of the contaminated water is measured by using a thermometer and the conductivity of the contaminated water is calculated from the measured resistance across the cell. Conductivity cells can be equipped with devices which electronically convert the measured resistance to conductivity and display the result on an electronic readout. If the conductivity of the contaminated water is significantly higher than the conductivity of distilled water at the same temperature it is known that significant ionic contamination is present in the oil being tested.

It should be noted that the separating step can be eliminated by using a surfactant, such as everyday dishwashing detergent.

According to this alternative method, a sample of the oil to be tested is isolated and an approximately equal amount of distilled water is obtained. The distilled water, a relatively small amount of the surfactant, and the oil sample are mixed to form an oil in water emulsion. The conductivity of the emulsion is measured directly by inserting a conductivity probe into the emulsion or by any other suitable means of determining conductivity.

An example of utilizing the foregoing alternative method is to isolate approximately 5 milliliters each of distilled water and an oil sample. The distilled water is placed in a test tube of approximately 25 milliliters and a drop of surfactant is added to this distilled water. The amount of surfactant added is between 0.05 milliliters and 0.15 milliliters. After the surfactant is added to the distilled water, the oil sample is added and the ingredients are mixed to obtain an oil in water emulsion. The ingredients can be mixed by vigorously shaking the test tube for about 10 seconds or any other method of mixing can be used which is capable of forming an oil in water emulsion. The conductivity of the contaminated water in the emulsion is determined directly by using a conductivity probe. One way of using the probe is to insert it in the distilled water with surfactant prior to adding the oil sample. The probe is inserted prior to adding the oil sample to prevent the probe from becoming coated with oil prior to mixing and thereby giving a false conductivity reading after the emulsion is formed. Alternatively, the probe can be inserted after the emulsion is formed.

The use of the surfactant makes it unnecessary to separate the distilled water, having the ionic contaminants dissolved therein, from the oil in water emulsion. Also, no heating of the distilled water or oil sample is necessary, but it is preferable to mix these substances at a temperature of approximately 70° F. to facilitate the mixing. The surfactant enhances the mixing process by increasing the surface area of contact between the oil and the distilled water. Also, the surfactant prevents the oil and water from separating and allows the distilled water with ionic contaminants to migrate through the oil in water emulsion to give a valid conductivity measurement.

The amount of surfactant to use in a particular situation depends on the type of oil being tested and the kind of surfactant which is used. Also, it is important that the proper amount of surfactant be used for the particular oil sample size being tested. Too little surfactant results in not enough surface contact between the oil and the distilled water. This prevents the wetting necessary for the proper dissolution of ionic contaminants from the oil sample into the distilled water and reduces the mobility of the dissolved ionic contaminants. Too much surfactant prevents the oil sample from properly interacting with the distilled water. That is, a third phase of surfactant might be formed preventing the distilled water from fully contacting the oil sample. Therefore, the amount of surfactant used should be kept within relatively defined limits. If approximately equal amounts of distilled water and oil are to be mixed then an amount of conventional surfactant approximately equal to one to three percent by volume of the oil sample size should be used.

The conductivity of the oil in water emulsion is a function of time. A transient state exists for the first few minutes after the emulsion is formed until a steady-state situation is reached. In the example discussed above, the steady-state is reached after approximately three minutes when using an oil sample of 5 milliliters. The transient state is attributed to the mobility of the ionic contaminants in the emulsion. It takes some time for the current flow to stabilize as the ionic contaminants begin to migrate between the electrodes of the conductivity probe. However, the relative conductivity at a given time accurately represents the level of ionic contamination of the oil sample. That is, a particular oil sample having a high concentration of ionic contaminants will give a higher conductivity reading than an oil sample, at the same temperature, having a lower concentration of ionic contaminants even if the conductivity determination is made during the transient state. This transient state must be considered since the absolute value of conductivity is dependent upon the time at which the measurement is taken. Therefore, if conductivity measurements are to be compared then they must be made after the steady state is reached or they must be adjusted to compensate for the transient state. One way of making this adjustment is to take all conductivity readings at the same fixed time after an emulsion is formed.

The Figure shows a graph of the conductivity of distilled water having hydrogen chloride or iron chloride dissolved therein as a function of chloride concentration and as a function of temperature. Assuming that a particular kind of chloride is present in the particular contaminated water sample under consideration the conductivity and temperature of the sample can be used with the graph to directly determine the chloride concentration in the sample. If the sample is at a temperature which is not shown on the graph it is necessary to interpolate between the temperature curves which are shown to determine the chloride concentration level. Thus, for example, assuming that hydrogen chloride is the ionic contaminant a conductivity of 800 micromhos/cm at a sample temperature of 77° F. indicates that there is 90.0 PPM of hydrogen chloride in the sample being tested.

It should be noted that hydrogen chloride is an ionic contaminant which results in a relatively high conductivity at relatively low concentrations in distilled water. Thus, a high conductivity level reliably indicates the presence of hydrogen chloride in the refrigerant of a refrigeration system of the type which is not likely to have significant amounts of other kinds of ionic contaminants. This type of refrigeration system is fairly typical since most refrigeration systems are designed to operate with pure refrigerant in a closed system. For example, it is unlikely that sufficient amounts of metal chlorides will be formed due to a mechanical failure to result in a high conductivity level unless the mechanical failure is of such extent that it is obvious from the operation of the refrigeration system that this type of failure has occurred. Therefore, by a process of elimination it can be determined that hydrogen chloride is the most probable ionic contaminant.

Also, it should be noted that there may be a certain amount of background ionic contaminants which are always present in the refrigerant of a particular refrigeration system. Therefore, it may be desirable to make a series of conductivity determinations at different times within a selected time interval to average out the effects of these background contaminants. The conductivity values are averaged to determine the average change in concentration of ionic contaminants within the selected time interval. An increase in conductivity as a function of time indicates an increasing concentration of ionic contaminants. Thus, a problem within the refrigeration system is detected even though a single conductivity determination may be high because of background ionic contaminants and therefore not reliably indicate a problem.

The following case histories illustrate how the method of testing compressor lubricating oil for ionic contaminants, according to the principles of the present invention, can be used to test a refrigeration system for certain malfunctions. Four samples of Mobil DTE 26 oil from centrifugal refrigeration machines were analyzed. Sample A was from a machine which had a bearing failure. Sample B was from a machine which had chronic water leaks. Sample C was from a machine which was just beginning to show water leaks. Sample D was a new, unused oil sample. Each of the four samples was tested in the same manner. First, a standard oil analysis was used to determine the chloride content, PH, viscosity, pure water content, acid number, and carboxylic content of the oil. The chloride concentration was determined by using precise amounts of oil and water which were mixed with silver nitrate to result in silver chloride formation. The silver chloride was filtered and then dried and weighed. This process is quite complicated and time consuming. However, it is a reliable method of determining chloride content. Viscosity was measured using a "Sayboldt Seconds Universal" test. Pure water content was determined using a water activated electrode test. It is interesting to note that pure water content did not correlate with chloride concentration. This can be explained by the fact that it is the presence of excess water in refrigerant which results in chloride formation. That quantity of pure water which is absorbed by the refrigerant does not result in chloride formation. Carboxylic content was determined using a conventional infra-red absorption technique. Also, PH and acid number were measured using conventional techniques.

After the standard oil analysis was concluded, 50 grams of each of the oil samples were tested for ionic contaminants according to the method of the present invention described previously. Specifically, for each oil sample, an equal weight of distilled water at approximately 200° F. was mixed in a separatory funnel with the oil. A portion of the contaminated water was extracted by holding the mixture stationary in the separatory funnel to allow the contaminated water to settle out and then this contaminated water was filtered through Whatman #42 filter paper to remove residual oil. The contaminated water portion was then placed in a standard conductivity cell and its conductance in micro-mhos/centimeter determined at a temperature of 77° F.

TABLE

| | A<br>Test Mach.<br>after<br>bearing<br>failure | B<br>Test Mach.<br>after<br>chronic<br>$H_2O$ leaks | C<br>Test Mach.<br>just beginning to show<br>$H_2O$ leaks | D<br>New<br>unused<br>oil |
|---|---|---|---|---|
| Michro-mhos/cm @ 77° F. | 152.8 | 490.0 | 77.0 | 16.9 |
| Chlorides, PPM | 18.0 | 85.3 | 0.7 | — |
| PH @ 77° F. | 7.155 | 7.237 | 7.265 | 6.100 |
| S.S.U. Visc. @ 100° F. | 305 | 320 | 321 | — |
| $H_2O$ PPM | 122 | 130 | 151 | — |
| Acid No. | 1.35 | 1.48 | 1.13 | — |
| I.R. Carboxylic | Low | Low | Low | — |

As shown in the table conductivity correlates very well with the chloride concentration which, in turn, is a reliable indicator of a problem within the refrigeration system. It should be noted that the new unused oil, sample D, resulted in a low conductivity level. Also, it should be noted that sample A, which was obtained from a machine with a bearing failure, while exhibiting a relatively high conductivity level relative to sample D, exhibited a low conductivity level relative to sample B, which was obtained from a machine with chronic water leaks. Thus, a very high conductivity level reliably indicates a water leak since the bearing failure sample A did not approach the conductivity level associated with the chronic water leak. This is because a bearing failure typically results in the formation of metal chlorides while a chronic water leak results in the formation of hydrogen chloride. The conductivity of a metal chloride solution is significantly less than the conductivity of a hydrogen chloride solution when equal amounts of each substance are dissolved in distilled water at the same temperature. Other types of ionic contaminants are not likely to be present in a closed refrigeration system. Thus, when a very high conductivity reading is obtained there is a high probability that the refrigeration system has a significant water leak.

Also, referring to the table, sample A and sample C exhibit conductivity levels of an intermediate level. If such an intermediate conductivity level is detected further investigation is necessary to determine whether the machine has a bearing problem or is just beginning to show a water leak. The other standard oil analysis parameters are included in the table to show further characteristics of the oil samples which were tested and to show that these parameters do not correlate with chloride concentration as well as conductance correlates with chloride concentration.

The preceding case histories and detailed description relate to testing for ionic contaminants in the lubricating oil for a compressor drive of a refrigeration system. However, it will be appreciated by one of ordinary skill in the art that the above method can be used to test for ionic contaminants in any oil which normally is in a pure state and where ionic contaminants are indicative of a malfunction of the system in which the oil is used. Therefore, while the present invention has been described in connection with particular embodiments, it is to be understood that various other embodiments and modifications may be made without departing from the scope of the invention heretofore described and claimed in the appended claims.

What is claimed is:

1. A method of testing oil for ionic contamination which comprises the steps of:
    isolating a sample of the oil to be tested;
    mixing the oil sample with an approximately equal weight of distilled water to dissolve ionic contaminants in the oil sample into the distilled water;
    separating a portion of the water with the ionic contaminants dissolved therein from the oil sample;
    filtering the separated portion of contaminated water to remove residual oil from this portion of the contaminated water;
    determining the conductivity of the separated portion of the contaminated water; and
    comparing the conductivity of the contaminated water to the conductivity of distilled water at the same temperature to determine the overall level of ionic contamination of the oil.

2. The method as recited in claim 1, which further comprises bringing the oil sample to a temperature of approximately 70° F. or above and bringing an approximately equal weight of distilled water to a temperature of approximately 200° F. prior to the step of mixing the oil sample with the distilled water.

3. A method of testing for ionic contaminants in the refrigerant of a refrigeration system of the type having a compressor drive which is lubricated with oil wherein there is contact between refrigerant from the refrigeration system and the compressor drive lubricating oil, which comprises the steps of:
    taking a sample of the compressor lubricating oil;
    mixing the oil sample with an approximately equal weight of distilled water to dissolve ionic contaminants in the oil sample into the distilled water;
    separating a portion of the water with the ionic contaminants dissolved therein from the oil sample;
    determining the conductivity of the separated portion of the contaminated water; and
    comparing the conductivity of the contaminated water to the conductivity of distilled water at the same temperature to determine the level of ionic contamination of the refrigerant of the refrigeration system.

4. The method as recited in claim 3, which further comprises the steps of:
    taking other samples of the compressor lubricating oil at different times within a selected time period;
    repeating the steps of mixing, separating, determining and comparing for each of these other samples; and
    determining the average change in the level of ionic contamination of the refrigerant of the refrigeration system during the selected time period.

5. The method as recited in claims 3 or 4 which further comprises:
    bringing the oil sample to a temperature of approximately 70° F. or above and bringing an approximately equal weight of distilled water to a temperature of approximately 200° F. prior to the step of mixing the oil sample with the distilled water.

6. The method as recited in claims 3 or 4, which further comprises:
    filtering the portion of contaminated water, after it has been separated from the oil sample and before its conductivity is determined, to remove residual oil from this portion of contaminated water.

7. The method as recited in claim 5 which further comprises:
    filtering the portion of contaminated water, after it has been separated from the oil sample and before its conductivity is determined, to remove residual oil from this portion of contaminated water.

8. A method of testing for ionic contaminants in the refrigerant of a refrigeration system of the type having a compressor drive which is lubricated with oil wherein there is contact between refrigerant from the refrigeration system and the compressor drive lubricating oil, which comprises the steps of:
    isolating a sample of the oil to be tested;
    mixing a surfactant, an amount of distilled water approximately equal in volume to the oil sample, and the oil sample to form an oil in water emulsion;
    determining the conductivity of the emulsion; and
    comparing the conductivity of the emulsion to the conductivity of distilled water at the same temperature to determine the level of ionic contamination of the oil.

9. The method as recited in claim 8 wherein the amount of surfactant used is sufficient to provide enough surface contact between the oil and the distilled water to form a complete oil in water emulsion but is less than the amount which would prevent portions of the distilled water and oil from coming into contact.

10. The method as recited in claim 8 wherein the amount of surfactant used is approximately one to three percent by volume of the amount of the oil sample.

11. The method as recited in claims 8, 9 or 10, which further comprises the steps of:
 taking other samples of the compressor lubricating oil at different times within a selected time period;
 repeating the steps of isolating, mixing, determining, and comparing for each of these other samples; and
 determining the average change in the level of ionic contamination of the refrigerant of the refrigeration system during the selected time period.

12. The method as recited in claims 8, 9 or 10, which further comprises the steps of:
 inserting a conductivity probe in the emulsion after it is formed; and
 allowing the emulsion to achieve a steady-state flow of ionic contaminants between the electrodes of the conductivity probe prior to determining the conductivity of the emulsion by using the probe.

13. The method as recited in claim 11 which further comprises the steps of:
 inserting a conductivity probe in the emulsion after it is formed; and
 allowing the emulsion to achieve a steady-state flow of ionic contaminants between the electrodes of the conductivity probe prior to determining the conductivity of the emulsion by using the probe.

* * * * *